(12) United States Patent
Blacker et al.

(10) Patent No.: US 6,545,188 B2
(45) Date of Patent: Apr. 8, 2003

(54) TRANSFER HYDROGENATION PROCESS AND CATALYST

(75) Inventors: Andrew John Blacker, Huddersfield (GB); Ben James Mellor, Grangemouth (GB)

(73) Assignee: Avecia Limited, Manchester (GB)

( * ) Notice: Subject to any disclaimer, the term of this patent is extended or adjusted under 35 U.S.C. 154(b) by 0 days.

(21) Appl. No.: 10/083,391

(22) Filed: Feb. 27, 2002

(65) Prior Publication Data

US 2002/0156282 A1 Oct. 24, 2002

Related U.S. Application Data

(62) Division of application No. 09/381,160, filed as application No. PCT/GB98/00862 on Mar. 20, 1998, now Pat. No. 6,372,931.

(30) Foreign Application Priority Data

Mar. 26, 1997 (GB) .............................. 9706321

(51) Int. Cl.$^7$ ..................... C07C 29/14; C07C 29/143
(52) U.S. Cl. .................... 568/814; 568/61; 568/715; 564/463
(58) Field of Search ................. 568/715, 814, 568/61; 564/463

(56) References Cited

U.S. PATENT DOCUMENTS

| | | | | |
|---|---|---|---|---|
| 4,208,539 A | * | 6/1980 | Rashkin | 568/814 |
| 5,237,088 A | * | 8/1993 | Weigert | 558/455 |
| 5,693,820 A | * | 12/1997 | Helmchen et al. | 548/101 |

OTHER PUBLICATIONS

Grotjahn et al, J.A.C.S., 116:6969–6970 (1994).
CA:112:198744 abs of Chem Ber by Kraemer et al. 123(4) pp. 767–778 (1990).
CA:120:31229 abs of DE 4127353 (1993).
CA:120:218107 abs of Chem Ber by Kramer et al. 126(11) pp. 2421–2427 (1993).
CA:114:24101 abs of J. Organomet. Chem. by Hermann et al. 394(1–3) pp. 285–303 (1990).
CA:123:56231 abs of Z Naturforsch B Chem Sci 50(3) pp. 394–404 (1995).
CA:109:5839 abs of Technol Rep Kansai UNiv by Nakano et al 29 pp 69–76 1987.*
CA:132:22748 abs of JP11335385 Dec. 1999.*
CA:130:296464 abs of Journal of Organic Chemistry by Murata et al 64(7) pp 2186–2187 1999.*
CA:115:158616 abs of J Chem Soc CHem Commun by Chowdhury et al 16 pp 1063–1064 1991.*

* cited by examiner

*Primary Examiner*—Jean F. Vollano
(74) *Attorney, Agent, or Firm*—Pillsbury Winthrop LLP

(57) ABSTRACT

A catalytic transfer hydrogenation process is provided. The catalyst employed in the process is a metal cyclopentadienyl complex which is coordinated to defined bidentate ligands. Preferred metals include rhodium, ruthenium and iridium. Preferred bidentate ligands are diamines and aminoalcohols, particularly those comprising chiral centers. The hydrogen donor is advantageously a secondary alcohol or a mixture of triethylamine and formic acid. The process can be employed to transfer hydrogenate ketones and imines, which are preferably prochiral. Catalysts for use in such a process are also provided.

22 Claims, No Drawings

TRANSFER HYDROGENATION PROCESS AND CATALYST

CROSS REFERENCE TO RELATED APPLICATIONS

This application is a divisional application based on U.S. Ser. No. 09/381,160, filed Nov. 9, 1999, now U.S. Pat. No. 6,372,931 B1, which is a National Phase application based on PCT/GB98/00862, filed Mar. 20, 1998, and which further claims priority from British Application No. 9706321.8, filed Mar. 26, 1997. These applications are incorporated in their entirety by reference herein.

This invention relates to catalytic transfer hydrogenation, particularly in the presence of a complexed transition metal, to a catalyst for such hydrogenation and to a process of making optically active compounds.

Hydrogenation by hydrogen transfer using catalysts containing phosphorus- or nitrogen-ligands was reviewed at length by Zassinovich et al. in Chem. Rev., 1992, 92, 1051–1069. These authors concluded 'in spite of excellent achievements, much work remains to be done'.

Transfer hydrogenation using catalysts in which the transition metal is coordinated to a benzenoid hydrocarbon have been explored. The following publications are of interest:

(1) Noyori et al., J. A. C. S., 1995, 117, 7562–7563: which discloses that use of chloro-ruthenium-mesitylene-N-monotosyl-1,2-diphenylethylenediamine as catalyst in the transfer hydrogenation of acetophenone to 1-phenylethanol by propan-2-ol gave up to a 95% yield of product having 97% enantiomeric excess. Similar results were obtained starting from other alkylaryl ketones. The efficiency of corresponding catalyst containing benzene in place of mesitylene was more sensitive to substituents on the aryl group of the starting ketone. Reaction times were generally rather long, typically 15 h; at longer reaction times stereoselectivity decreased, apparently owing to reverse hydrogenation. No turnover numbers are reported. The authors commented that 'the overall catalytic performance is unable to rival that of the current best hydrogenation method' as described in an earlier publication by themselves.

(2) Noyori et al., J. Chem. Soc. Chem. Commun., 1996, 233–234: which discloses that catalysts similar to those of Noyori et al. (1) above but containing other alkylbenzene ligands and various beta-amino alcohols in place of the diphenylethylenediamine were to differing extents effective in the hydrogenation of acetophenone. The beta-amino alcohol ligand gave greater catalyst stability. The preferred arene ligand was hexamethylbenzene. Turnover numbers were up to 227 moles of product per mole of catalyst per hour.

(3) Noyori et al., J. A. C. S., 1996, 118, 2521–2522: which discloses that to prevent reverse hydrogen transfer in the process of Noyori et al. (1) above, formic acid-triethylamine was used as hydrogen source. Reaction times mainly over 14 h and up to 90 h were used; no turnover numbers are reported.

(4) Noyori et al., J. A. C. S., 1996, 118, 4916–4917: which discloses that the process of Noyori et al. (3) above is effective for reduction of imines (especially cyclic imines) to enantioselected amines.

These processes appear to require relatively long cycle times. As well as involving uneconomic utilisation of chemical plant, such slow reaction can lead to decomposition of the catalytic complex and slow loss of product optical purity; also it affords limited scope for adjusting reaction conditions such as temperature and reactant concentration to maximise the difference in rate between enantiomerically wanted and unwanted reactions.

Besides the phosphorus-, nitrogen- and benzene-ligated transition metals, complexes based on pentamethylcyclopentadienyl (hereinafter Cp*) have been shown to be effective as catalysts in homogeneous hydrogenation of olefins by free hydrogen (Maitlis, Acc. Chem. Res., 1978, 11, 301–307; Maitlis et al., J. Chem. Soc. Dalton, 1978, 617–626); there was no disclosure of hydrogen transfer in the absence of free hydrogen or of catalysts containing a chelating or chiral-directing ligand.

Complexes of iridium with Cp* and acylated or sulphonylated alpha amino carboxylic acid have been described by Grotjahn et al. (J. A. C. S., 1994, 116, 6969–6970) but without evidence of catalytic activity. Complexes of rhodium with Cp* and 2,2,-bipyridyls and the use of these with formate to hydrogenate nicotinamide adenine dinucleotide (NAD) to NADH have been described by Steckhan et al. (Angew. Chem. Int. Ed. Engl., 1990, 29(4), 388–390). Turnover frequencies up to 67.5 per h are reported, but no activity after 100 catalytic cycles.

We have now found that stereoselective transfer hydrogenation can be efficiently carried out by means of a catalyst comprising a complex of a transition metal, a chelating ligand and a cyclopentadienyl group.

According to a first aspect of the present invention there is provided a process for the transfer hydrogenation of a compound of formula (1) to produce a compound of formula (2)

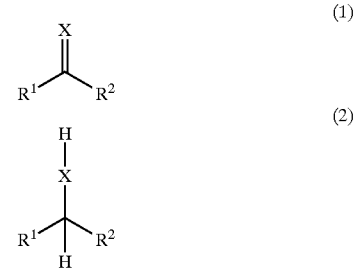

wherein:

X represents $CR^3R^4$, $NR^5$, $(NR^5R^6)^+Q^-$, O or S;

$R^1$, $R^2$, $R^3$, $R^4$, $R^5$ and $R^6$ each independently represents a hydrogen atom, an optionally substituted hydrocarbyl, a perhalogenated hydrocarbyl or an optionally substituted heterocyclyl group, one or more of $R^1$ & $R^2$, $R^1$ & $R^3$, $R^2$ & $R^4$, $R^3$ & $R^4$, $R^1$ & $R^5$, $R^2$ & $R^6$ and $R^5$ & $R^6$ optionally being linked in such a way as to form an optionally substituted ring(s); and $Q^-$ represents an anion;

said process comprising reacting the compound of formula (1) with a hydrogen donor in the presence of a catalyst, characterised in that the catalyst has the general formula:

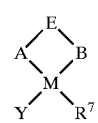

wherein:

$R^7$ represents an optionally substituted cyclopentadienyl group;

A represents —NR$^8$—, —NR$^9$—, —NHR$^8$ or —NR$^8$R$^9$ where R$^8$ is H, C(O)R$^{10}$, SO$_2$R$^{10}$, C(O)NR$^{10}$R$^{14}$, C(S)NR$^{10}$R$^{14}$, C(=NR$^{14}$)SR$^{15}$ or C(=NR$^{14}$)OR$^{15}$, R$^9$ and R$^{10}$ each independently represents an optionally substituted hydrocarbyl, perhalogenated hydrocarbyl or an optionally substituted heterocyclyl group, and R$^{14}$ and R$^{15}$ are each independently hydrogen or a group as defined for R$^{10}$;

B represents —O—, —OH, OR$^{11}$, —S—, —SH, SR$^{11}$, —NR$^{11}$—, —NR$^{12}$—, —NHR$^{12}$ or —NR$^{11}$R$^{12}$ where R$^{12}$ is H, C(O)R$^{13}$, SO$_2$R$^{13}$, C(O)NR$^{13}$R$^{16}$, C(S)NR$^{13}$R$^{16}$, C(=NR$^{16}$)SR$^{17}$ or C(=NR$^{16}$)OR$^{17}$, R$^{11}$ and R$^{13}$ each independently represents an optionally substituted hydrocarbyl, perhalogenated hydrocarbyl or an optionally substituted heterocyclyl group, and R$^{16}$ and R$^{17}$ are each independently hydrogen or a group as defined for R$^{13}$;

E represents a linking group;

M represents a metal capable of catalysing transfer hydrogenation; and

Y represents an anionic group, a basic ligand or a vacant site;

provided that when Y is not a vacant site that at least one of A or B carries a hydrogen atom.

The catalytic species is believed to be substantially as represented in the above formula. It may be introduced on a solid support.

Hydrocarbyl groups which may be represented by R$^{1-6}$, R$^9$, R$^{10}$, R$^{11}$ and R$^{13-17}$ independently include alkyl, alkenyl and aryl groups, and any combination thereof, such as aralkyl and alkaryl, for example benzyl groups.

Alkyl groups which may be represented by R$^{1-6}$, R$^9$, R$^{10}$, R$^{11}$ and R$^{13-17}$ include linear and branched alkyl groups comprising up to 20 carbon atoms, particularly from 1 to 7 carbon atoms and preferably from 1 to 5 carbon atoms. When the alkyl groups are branched, the groups often comprising up to 10 branch chain carbon atoms, preferably up to 4 branch chain atoms. In certain embodiments, the alkyl group may be cyclic, commonly comprising from 3 to 10 carbon atoms in the largest ring and optionally featuring one or more bridging rings. Examples of alkyl groups which may be represented by R$^{1-6}$, R$^9$, R$^{10}$, R$^{11}$ and R$^{13-17}$ include methyl, ethyl, propyl, 2-propyl, butyl, 2-butyl, t-butyl and cyclohexyl groups.

Alkenyl groups which may be represented by R$^{1-6}$, R$^9$, R$^{10}$, R$^{11}$ and R$^{13-17}$ include C$_{2-20}$, and preferably C$_{2-6}$ alkenyl groups. One or more carbon—carbon double bonds may be present. The alkenyl group may carry one or more substituents, particularly phenyl substituents. Examples of alkenyl groups include vinyl, styryl and indenyl groups. When either of R$^1$ or R$^2$ represents an alkenyl group, a carbon—carbon double bond is preferably located at the position β to the C=X moiety. When either of R$^1$ or R$^2$ represents an alkenyl group, the compound of formula (1) is preferably an α, β-unsaturated ketone.

Aryl groups which may be represented by R$^{1-6}$, R$^9$, R$^{10}$, R$^{11}$ and R$^{13-17}$ may contain 1 ring or 2 or more fused rings which may include cycloalkyl, aryl or heterocyclic rings. Examples of aryl groups which may be represented by R$^{1-6}$, R$^9$, R$^{10}$, R$^{11}$ and R$^{13-17}$ include phenyl, tolyl, fluorophenyl, chlorophenyl, bromophenyl, trifluoromethylphenyl, anisyl, naphthyl and ferrocenyl groups.

Perhalogenated hydrocarbyl groups which may be represented by R$^{1-6}$, R$^9$, R$^{10}$, R$^{11}$ and R$^{13-17}$ independently include perhalogenated alkyl and aryl groups, and any combination thereof, such as aralkyl and alkaryl groups.

Examples of perhalogenated alkyl groups which may be represented by R$^{1-6}$, R$^9$, R$^{10}$, R$^{11}$ and R$^{13-17}$ include —CF$_3$ and —C$_2$F$_5$.

Heterocyclic groups which may be represented by R$^{1-6}$, R$^9$, R$^{10}$, R$^{11}$ and R$^{13-17}$ independently include aromatic, saturated and partially unsaturated ring systems and may constitute 1 ring or 2 or more fused rings which may include cycloalkyl, aryl or heterocyclic rings. The heterocyclic group will contain at least one heterocyclic ring, the largest of which will commonly comprise from 3 to 7 ring atoms in which at least one atom is carbon and at least one atom is any of N, O, S or P. When either of R$^1$ or R$^2$ represents or comprises a heterocyclic group, the atom in R$^1$ or R$^2$ bonded to the C=X group is preferably a carbon atom. Examples of heterocyclic groups which may be represented by R$^{1-6}$, R$^9$, R$^{10}$, R$^{11}$ and R$^{13-17}$ include pyridyl, pyrimidyl, pyrrolyl, thiophenyl, furanyl, indolyl, quinolyl, isoquinolyl, imidazoyl and triazoyl groups.

When any of R$^{1-6}$, R$^9$, R$^{10}$, R$^{11}$ and R$^{13-17}$ is a substituted hydrocarbyl or heterocyclic group, the substituent(s) should be such so as not to adversely affect the rate or stereoselectivety of the reaction. Optional substituents include halogen, cyano, nitro, hydroxy, amino, thiol, acyl, hydrocarbyl, perhalogentated hydrocarbyl, heterocyclyl, hydrocarbyloxy, mono or di-hydrocarbylamino, hydrocarbylthio, esters, carbonates, amides, sulphonyl and sulphonamido groups wherein the hydrocarbyl groups are as defined for R$^1$ above. One or more substituents may be present.

When any of R$^1$ & R$^2$, R$^1$ & R$^3$, R$^2$ & R$^4$, R$^3$ & R$^4$, R$^1$ & R$^5$, R$^2$ & R$^6$, and R$^5$ & R$^6$ are linked in such a way that when taken together with either the carbon atom and/or atom X of the compound of formula (1) that a ring is formed, it is preferred that these be 5, 6 or 7 membered rings. Examples of such compounds of formula (1) include 3,4-dihydroisoquinoline, 1-tetralone, 2-tetralone, 4-chromanone, 1-methyl-6,7-dimethoxy-3,4-dihydroisoquinoline, 1-benzosubarone, 2-indanone and 1-indanone.

Compounds of formula (1) where X is represented by NR$^5$ or (NR$^5$R$^6$)$^+$Q$^-$, include imines or iminium salts. Where a compound of formula (1) is an imine, it may optionally be converted to an iminium salt. Iminium salts are preferred over imines. Preferred iminium salts are represented by compounds of formula (1) in which X is (NR$^5$R$^6$)$^+$ Q$^-$ such that either R$^5$ or R$^6$ are hydrogen but that R$^5$ or R$^6$ are not identical. When the compound of formula (1) is an iminium salt, an anion represented by Q$^-$ is present. Examples of anions which may be present are halide, hydrogen sulphate, tosylate, formate, acetate, tetrafluoroborate, trifluoromethanesulphonate and trifluoroacetate.

X is most preferably O.

In certain preferred embodiments, R$^1$ and R$^2$ are both independently C$_{1-6}$ alkyl, both independently aryl, particularly phenyl, or one is aryl, particularly phenyl and one is C$_{1-6}$ alkyl. Substituents may be present, particularly substituents para to the C=X group when one or both of R$^1$ and R$^2$ is a phenyl group.

Most advantageously, the compound of formula (1) is prochiral, such that the hydrogenated product of formula (2) comprises a chiral atom to which R$^1$, R$^2$ and X are each bonded. Such an asymmetric transfer hydrogenation process forms an especially preferred aspect of the present invention. Most commonly, when the compound of formula (1) is prochiral, R$^1$ and R$^2$ are different, and neither is hydrogen. Usefully, one of R$^1$ and R$^2$ is aliphatic and the other is aryl or heterocyclyl.

Examples of compounds of formula (1) include acetophenone, 4-chloroacetophenone, 4-methoxyacetophenone, 4-trifluoromethylacetophenone, 4-nitroacetophenone, 2-chloroacetophenone and acetophenone benzylimine.

Hydrogen donors include hydrogen, primary and secondary alcohols, primary and secondary amines, carboxylic acids and their esters and amine salts, readily dehydrogenatable hydrocarbons, clean reducing agents, and any combination thereof.

Primary and secondary alcohols which may be employed as hydrogen donors comprise commonly from 1 to 10 carbon atoms, preferably from 2 to 7 carbon atoms, and more preferably 3 or 4 carbon atoms. Examples of primary and secondary alcohols which may be represented as hydrogen donors include methanol, ethanol, propan-1-ol, propan-2-ol, butan-1-ol, butan-2-ol, cyclopentanol, cyclohexanol, benzylalcohol, and menthol. When the hydrogen donor is an alcohol, secondary alcohols are preferred, especially propan-2-ol and butan-2-ol.

Primary and secondary amines which may be employed as hydrogen donors comprise commonly from 1 to 20 carbon atoms, preferably from 2 to 14 carbon atoms, and more preferably 3 or 8 carbon atoms. Examples of primary and secondary amines which may be represented as hydrogen donors include ethylamine, propylamine, isopropylamine, butylamine, isobutylamine, hexylamine, diethylamine, dipropylamine, di-isopropylamine, dibutylamine, di-isobutylamine, dihexylamine, benzylamine, dibenzylamine and piperidine. When the hydrogen donor is an amine, primary amines are preferred, especially primary amines comprising a secondary alkyl group, particularly isopropylamine and isobutylamine.

Carboxylic acids or their esters which may be employed as hydrogen donors comprise commonly from 1 to 10 carbon atoms, preferably from 1 to 3 carbon atoms. In certain embodiments, the carboxylic acid is advantageously a beta-hydroxy-carboxylic acid. Esters may be derived from the carboxylic acid and a $C_{1-10}$ alcohol. Examples of carboxylic acids which may be employed as hydrogen donors include formic acid, lactic acid, ascorbic acid and mandelic acid. When a carboxylic acid is employed as hydrogen donor, at least some of the carboxylic acid is preferably present as an amine salt or ammonium salt. Amines which may be used to form such salts include both aromatic and non-aromatic amines, also primary, secondary and tertiary amines and comprise typically from 1 to 20 carbon atoms. Tertiary amines, especially trialkylamines, are preferred. Examples of amines which may be used to form salts include trimethylamine, triethylamine, di-isopropylethylamine and pyridine. The most preferred amine is triethylamine. When at least some of the carboxylic acid is present as an amine salt, particularly when a mixture of formic acid and triethylamine is employed, the mole ratio of acid to amine is commonly about 5:2. This ratio may be maintained during the course of the reaction by the addition of either component, but usually by the addition of the carboxylic acid.

Readily dehydrogenatable hydrocarbons which may be employed as hydrogen donors comprise hydrocarbons which have a propensity to aromatise or hydrocarbons which have a propensity to form highly conjugated systems. Examples of readily dehydrogenatable hydrocarbons which may be employed by as hydrogen donors include cyclohexadiene, cyclohexene, tetralin, dihydrofuran and terpenes.

Clean reducing agents which may be represented as hydrogen donors comprise reducing agents with a high reduction potential, particularly those having a reduction potential relative to the standard hydrogen electrode of greater than about −0.1 eV, often greater than about −0.5 eV, and preferably greater than about −1 eV. Examples of clean reducing agents which may be represented as hydrogen donors include hydrazine and hydroxylamine.

The most preferred hydrogen donors are propan-2-ol, butan-2-ol, triethylammonium formate and a mixture of triethylammonium formate and formic acid.

The optionally substituted cyclopentadienyl group which may be represented by $R^7$ includes cyclopentadienyl groups capable of eta-5 bonding. The cyclopentadienyl group is often substituted with from 1 to 5 hydrocarbyl groups, preferably with 3 to 5 hydrocarbyl groups and more preferably with 5 hydrocarbyl groups. Preferred hydrocarbyl substituents include methyl, ethyl and phenyl. When the hydrocarbyl substitutents contain enantiomeric and/or diastereomeric centres, it is preferred that the enantiomerically and/or diastereomerically purified forms of these are used. Examples of optionally substituted cyclopentadienyl groups include cyclopentadienyl, pentamethyl-cyclopentadienyl, pentaphenylcyclopentadienyl, tetraphenylcyclopentadienyl, ethyltetramethylpentadienyl, menthyltetraphenylcyclopentadienyl, neomenthyl-tetraphenylcyclopentadienyl, menthylcyclopentadienyl, neomenthylcyclopentadienyl, tetrahydroindenyl, menthyltetrahydroindenyl and neomenthyltetrahydroindenyl groups. Pentamethylcyclopentadienyl is especially preferred.

When either A or B is an amide group represented by —$NR^8$—, —$NHR^8$, $NR^8R^9$, —$NR^{12}$—, —$NHR^{12}$ or $NR^{11}R^{12}$ wherein $R^9$ and $R^{11}$ are as hereinbefore defined, and where $R^8$ or $R^{12}$ is an acyl group represented by —$C(O)R^{10}$ or —$C(O)R^{13}$, $R^{10}$ and $R^{13}$ independently are often linear or branched $C_{1-7}$alkyl, $C_{1-8}$-cycloalkyl or aryl, for example phenyl. Examples of acyl groups which may be represented by $R^8$ or $R^{12}$ include benzoyl, acetyl and halogenoacetyl, especially trifluoroacetyl, groups.

When either A or B is present as a sulphonamide group represented by —$NR^8$—, —$NHR^8$, $NR^8R^9$, —$NR^{12}$—, —$NHR^{12}$ or $NR^{11}R^{12}$ wherein $R^9$ and $R^{11}$ are as hereinbefore defined, and where $R^8$ or $R^{12}$ is a sulphonyl group represented by —$S(O)_2R^{10}$ or —$S(O)_2R^{13}$, $R^{10}$ and $R^{13}$ independently are often linear or branched $C_{1-8}$alkyl, $C_{1-8}$cycloalkyl or aryl, for example phenyl. Preferred sulphonyl groups include methanesulphonyl, trifluoromethanesulphonyl and especially p-toluenesulphonyl groups.

When either of A or B is present as a group represented by —$NR^8$—, —$NHR^8$, $NR^8R^9$, —$NR^{12}$—, —$NHR^{12}$ or $NR^{11}R^{12}$ wherein $R^9$ and $R^{11}$ are as hereinbefore defined, and where $R^8$ or $R^{12}$ is a group represented by $C(O)NR^{10}R^{14}$, $C(S)NR^{10}R^{14}$, $C(=NR^{14})SR^{15}$, $C(=NR^{14})OR^{15}$, $C(O)NR^{13}R^{16}$, $C(S)NR^{13}R^{16}$, $C(=NR^{16})SR^{17}$ or $C(=NR^{16})OR^{17}$, $R^{10}$ and $R^{13}$ independently are often linear or branched $C_{1-8}$alkyl, such as methyl, ethyl, isopropyl, $C_{1-8}$cycloalkyl or aryl, for example phenyl, groups and $R^{14-17}$ are often each independently hydrogen or linear or branched $C_{1-8}$alkyl, such as methyl, ethyl, isopropyl, $C_{1-8}$cycloalkyl or aryl, for example phenyl, groups.

It will be recognised that the precise nature of A and B will be determined by whether A and/or B are formally bonded to the metal or are coordinated to the metal via a lone pair of electrons.

The groups A and B are connected by a linking group E. The linking group E achieves a suitable conformation of A and B so as to allow both A and B to bond or coordinate to the metal, M. A and B are commonly linked through 2, 3 or 4 atoms. The atoms in E linking A and B may carry one or more substituents. The atoms in E, especially the atoms alpha to A or B, may be linked to A and B, in such a way as to form a heterocyclic ring, preferably a saturated ring, and particularly a 5, 6 or 7-membered ring. Such a ring may be fused to one or more other rings. Often the atoms linking A and B will be carbon atoms. Preferably, one or more of the carbon atoms linking A and B will carry substituents in addition to A or B. Substituent groups include those which may substitute $R^1$, as defined above. Advantageously, any such substituent groups are selected to be groups which do not coordinate with the metal, M. Preferred substituents include halogen, cyano, nitro, sulphonyl, hydrocarbyl, perhalogenated hydrocarbyl and heterocyclyl groups as defined above. Most preferred substituents are $C_{1-6}$ alkyl groups, and phenyl groups. Most preferably, A and B are linked by two carbon atoms, and especially an optionally substituted ethyl moiety. When A and B are linked by two carbon atoms, the two carbon atoms linking A and B may comprise part of an aromatic or aliphatic cyclic group, particularly a 5, 6 or 7-membered ring. Such a ring may be fused to one or more other such rings. Particularly preferred are embodiments in which E represents a 2 carbon atom separation and one or both of the carbon atoms carries an optionally substituted aryl group as defined above or E represents a 2 carbon atom separation which comprises a cyclopentane or cyclohexane ring, optionally fused to a phenyl ring.

E preferably comprises part of a compound having at least one stereospecific centre. Where any or all of the 2, 3 or 4 atom atoms linking A and B are substituted so as to define at least one stereospecific centre on one or more of these atoms, it is preferred that at least one of the stereospecific centres be located at the atom adjacent to either group A or B. When at least one such stereospecific centre is present, it is advantageously present in an enantiomerically purified state.

When B represents —O— or —OH, and the adjacent atom in E is carbon, it is preferred that B does not form part of a carboxylic group.

Compounds which may be represented by A—E—B, or from which A—E—B may be derived by deprotonation, are often aminoalcohols, including 4-aminoalkan-1-ols, 1-aminoalkan-4-ols, 3-aminoalkan-1-ols, 1-aminoalkan-3-ols, and especially 2-aminoalkan-1-ols, 1-aminoalkan-2-ols, 3-aminoalkan-2-ols and 2-aminoalkan-3-ols, and particularly 2-aminoethanols or 3-aminopropanols, or are diamines, including 1,4-diaminoalkanes, 1,3-diaminoalkanes, especially 1,2- or 2,3-diaminoalkanes and particularly ethylenediamines. Further aminoalcohols that may be represented by A—E—B are 2-aminocyclopentanols and 2-aminocyclohexanols, preferably fused to a phenyl ring. Further diamines that may be represented by A—E—B are 1,2-diaminocyclopentanes and 1,2-diaminocyclohexanes, preferably fused to a phenyl ring. The amino groups may advantageously be N-tosylated. When a diamine is represented by A—E—B, preferably at least one amino group is N-tosylated. The aminoalcohols or diamines are advantageously substituted, especially on the linking group, E, by at least one alkyl group, such as a $C_{1-4}$alkyl, and particularly a methyl, group or at least one aryl group, particularly a phenyl group.

Specific examples of compounds which can be represented by A—E—B and the protonated equivalents from which they may be derived are:

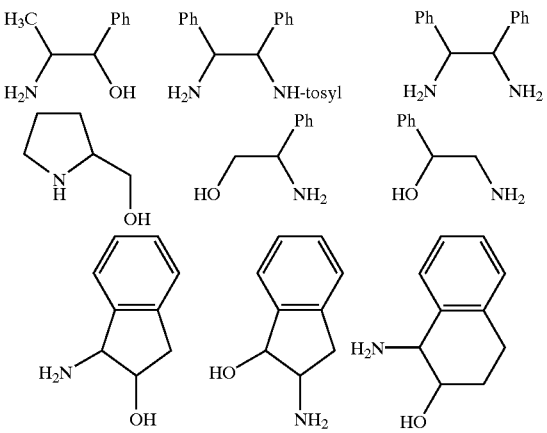

Preferably, the enantiomerically and/or diastereomerically purified forms of these are used. Examples include (1S,2R)-(+)-norephedrine, (1R,2S)-(+)-cis-1-amino-2-indanol, (1S,2R)-2-amino-1,2-diphenylethanol, (1S,2R)-(−)-cis-1-amino-2-indanol, N-tosyl-(1S,2R)-cis-1-amino-2-indanol, (1R,2S)-(−)-norephedrine, (S)-(+)-2-amino-1-phenylethanol, (1R,2S)-2-amino-1,2-diphenylethanol, (R)-(−)-2-pyrrolidinemethanol and (S)-(+)-2-pyrrolidinemethanol.

Metals which may be represented by M include metals which are capable of catalysing transfer hydrogenation. Preferred metals include transition metals, more preferably the metals in Group VIII of the Periodic Table, especially ruthenium, rhodium or iridium. When the metal is ruthenium it is preferably present in valence state II. When the metal is rhodium or iridium it is preferably present in valence state III.

Anionic groups which may be represented by Y include hydride, hydroxy, hydrocarbyloxy, hydrocarbylamino and halogen groups. Preferably when a halogen is represented by Y, the halogen is chloride. When a hydrocarbyloxy or hydrocarbylamino group is represented by Y, the group may be derived from the deprotonation of the hydrogen donor utilised in the reaction.

Basic ligands which may be represented by Y include water, $C_{1-4}$ alcohols, $C_{1-8}$ primary or secondary amines, or the hydrogen donor which is present in the reaction system. A preferred basic ligand represented by Y is water.

Most preferably, the nature of A—E—B, $R^7$ and Y are chosen such that the catalyst is chiral. When such is the case, an enantiomerically and/or diastereomerically purified form is preferably employed. Such catalysts are most advantageously employed in asymmetric transfer hydrogenation processes. In many embodiments, the chirality of the catalyst is derived from the nature of A—E—B.

The process is carried out preferably in the presence of a base, especially when Y is not a vacant site. The $pK_a$ of the base is preferably at least 8.0, especially at least 10.0. Convenient bases are the hydroxides, alkoxides and carbonates of alkali metals; tertiary amines and quaternary ammonium compounds. Preferred bases are sodium 2-propoxide and triethylamine. When the hydrogen donor is not an acid, the quantity of base used can be up to 5.0, commonly up to 3.0, often up to 2.5 and especially in the range 1.0 to 3.5, by moles of the catalyst. The substantial excesses of base used by Noyori et al. appear to be unnecessary. When the hydrogen donor is an acid, the catalyst is preferably contacted with a base prior to the introduction of the hydrogen donor. In such a case, the mole ratio of base to catalyst prior to the introduction of the hydrogen donor is often from 1:1 to 3:1, and preferably about 1:1.

Although gaseous hydrogen may be present, the process is normally operated in the absence of gaseous hydrogen since it appears to be unnecessary.

The absence of oxygen is not essential. This has been shown by carrying out the process with sparging of the reactor mixture with pure oxygen: the initial turnover rate was 500 h$^{-1}$ and in 2 hours a 40% conversion was obtained. However better results have been obtained under an inert atmosphere, initial rates for example of 1080 h$^{-1}$ in static nitrogen and 1500 h$^{-1}$ with nitrogen sparging. Advantageously, the process is carried out in the substantial absence of carbon dioxide.

When the product(s) from dehydrogenation of the hydrogen donor is volatile, for example boils at under 100° C., the removal of this volatile product is preferred. The removal can be accomplished by the use of inert gas sparging. More preferably, the removal is accomplished by distillation preferably at less than atmospheric pressure. When reduced pressure distillation is employed, the pressure is often no more than 500 mmHg, commonly no more than 200 mmHg, preferably in the range of from 5 to 100 mmHg, and most preferably from 10 to 80 mmHg.

Suitably the process is carried out at temperatures in the range of from minus 78 to plus 150° C., preferably from minus 20 to plus 110° C. and more preferably from minus 5 to plus 60° C. The initial concentration of the substrate, a compound of formula (1), is suitably in the range 0.05 to 1.0 and, for convenient larger scale operation, can be for example up to 6.0 more especially 0.75 to 2.0, on a molar basis. The molar ratio of the substrate to catalyst is suitably no less than 50:1 and can be up to 50000:1, preferably between 250:1 and 5000:1 and more preferably between 500:1 and 2500:1. The hydrogen donor is preferably employed in a molar excess over the substrate, especially from 5 to 20 fold or, if convenience permits, greater, for example up to 500 fold. Reaction times are typically in the range of from 1.0 min to 24 h, especially up to 8 h and conveniently about 3 h. It appears that substantially shorter times than those disclosed in the above-mentioned publications are made practicable by the invention. After reaction, the mixture is worked up by standard procedures. A reaction solvent may be present, for example acetonitrile or, conveniently, the hydrogen donor when the hydrogen donor is liquid at the reaction temperature, particularly when the hydrogen donor is a primary or secondary alcohol or a primary or secondary amine. Usually it is preferred to operate in substantial absence of water, but water does not appear to inhibit the reaction. If the hydrogen donor or the reaction solvent is not miscible with water and the desired product is water soluble, it may be desirable to have water present as a second phase extracting the product, pushing the equilibrium and preventing loss of product optical purity as the reaction proceeds. The concentration of substrate may be chosen to optimise reaction time, yield and enantiomeric excess.

According to a second embodiment of the present invention there is provided a catalyst of general formula:

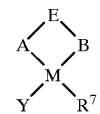

wherein:
R$^7$ represents an optionally substituted cyclopentadienyl group;

A represents —NR$^8$—, —NR$^9$—, —NHR$^8$, or —NR$^8$R$^9$ where R$^8$ is H, C(O)R$^{10}$, SO$_2$R$^{10}$, C(O)NR$^{10}$R$^{14}$, C(S) NR$^{10}$R$^{14}$, C(=NR$^{14}$)SR$^{15}$ or C(=NR$^{14}$)OR$^{15}$, R$^9$ and R$^{10}$ each independently represents an optionally substituted hydrocarbyl, perhalogenated hydrocarbyl or an optionally substituted heterocyclyl group, and R$^{14}$ and R$^{15}$ are each independently hydrogen or a group as defined for R$^{10}$;

B represents —O—, —OH, OR$^{11}$, —S—, —SH, SR$^{11}$, —NR$^{11}$—, —NR$^{12}$—, —NHR$^{12}$, or —NR$^{11}$R$^{12}$ where R$^{12}$ is H, C(O)R$^{13}$, SO$_2$R$^{13}$, C(O)NR$^{13}$R$^{16}$, C(S) NR$^{13}$R$^{16}$, C(=NR$^{16}$)SR$^{17}$ or C(=NR$^{16}$)OR$^{17}$, R$^{11}$ and R$^{13}$ each independently represents an optionally substituted hydrocarbyl, perhalogenated hydrocarbyl or an optionally substituted heterocyclyl group, and R$^{16}$ and R$^{17}$ are each independently hydrogen or a group as defined for R$^{13}$;

E represents a linking group;

M represents a metal capable of catalysing transfer hydrogenation; and

Y represents an anionic group, a basic ligand or a vacant site;

provided that (i) when Y is not a vacant site that at least one of A or B carries a hydrogen atom and (ii) when B represents —O— or —OH, that B is not part of a carboxylate group.

In the catalysts according to the present invention, A, E, B, M, R$^7$ and Y can be as described above for the transfer hydrogenation process.

The catalytic species is believed to be substantially as represented in the above formula. It may be employed as an oligomer or metathesis product, on a solid support or may be generated in situ.

In certain embodiments it has advantageously been found that certain catalysts are preferred in the transfer hydrogenation of certain substrate types. Catalysts in which A—E—B is derived from aminoalcohols, particularly norephedrine and cis-aminoindanol, are preferred in the transfer hydrogenation of aldehydes and ketones to give alcohols. Especially, M is also rhodium (III) and R$^7$ represents pentamethylcyclopentadienyl. Further, isopropanol is preferably employed as hydrogen donor and sodium isopropoxide is employed as a base. Catalysts in which A—E—B is derived from N-tosyldiamines are preferred in transfer hydrogenation reactions of imines and iminium salts. Especially, M is also rhodium (III) and R$^7$ represents pentamethylcyclopentadienyl. Further, sodium isopropoxide or triethylamine are often employed as a base. When the compound of formula (1) is an imine, a mixture of formic acid and triethylamine is preferably employed as hydrogen donor and when the compound of formula (1) is a preformed imminium salt, preferably a trifluoroacetate salt, isopropanol is preferably employed as hydrogen donor.

The catalyst can be made by reacting a metal cyclopentadienyl halide complex with a compound of formula A—E—B as defined above or a protonated equivalent from which it may be derived, and, where Y represents a vacant site, reacting the product thereof with a base. The metal cyclopentadienyl halide complex preferably has the formula $[MR^7Z_2]_2$, wherein M and $R^7$ are as defined above, and Z represents a halide, particularly chloride.

For the preparation of the catalysts according to the present invention, a solvent is preferably present. Suitable reaction temperatures are in the range 0–100, for example 20–70, °C., often giving reaction times of 0.5–5.0 h. After reaction is complete, the catalyst may if desired be isolated, but is more conveniently stored as the solution or used soon after preparation. The solution can contain the hydrogen donor and this, if a secondary alcohol, may be present in or used as the solvent for steps (a) and/or (b). The preparation and after-handling should preferably be under an inert atmosphere, and particularly in carbon dioxide and oxygen-free conditions.

The catalyst or catalyst solution is generally treated with base either just prior to use in a transfer hydrogenation reaction, or during use. This can be accomplished by adding base to the catalyst in solution, or to the compound of formula (1) in solution, or by addition to the transfer hydrogenation reaction.

Transfer hydrogenation can be accomplished by transferring the solution of catalyst to a solution of substrate, a compound of general formula I. Alternatively a solution of substrate can be added to a solution of catalyst. Base may be pre-added to the catalyst solution and/or the substrate solution, or can be added later. The hydrogen donor if not already present in the catalyst solution may be added to the substrate solution, or may be added to the reaction mixture.

The invention is illustrated by the following Examples.

Unless otherwise stated, % conversions and % enantiomeric excess (e.e.) were determined by GC.

EXAMPLE 1

Preparation of Catalyst and Reduction of Acetophenone

| Reactant | Wt used | Mol. Wt | Mol ratio | |
|---|---|---|---|---|
| $[Rh(Cp^*)Cl_2]_2$** | 0.0254 g | 618.08 | 1.0 | 41.2 µmol |
| (1S,2R)-(+)-Norephedrine | 0.0209 g | 151.21 | 3.36 | 138.2 µmol |
| 2-propanol (anhydrous) | 100 ml | 60.10 | 31677 | 1.305 mol |
| KOH 0.1 M in 2-propanol | 3.3 ml | 56.11 | 4.01 | 0.33 mmol |
| Acetophenone | 2.06 g | 120.15 | 209 | 17 mmol |

Notes: **purchased from STREM Chemicals
Prior to the reaction, the solvent was degassed: 100 ml of anhydrous 2-propanol was added by syringe to a sealed clean dry round bottomed flask and degassed in vacuo at under 20° C. for 30 min.

(a) Catalyst Preparation

The (+)-norephedrine and rhodium compound were weighed out into a clean dry Schlenk flask. The flask was stoppered with a 'Suba-seal' (RTM). Its contents were evacuated, then purged at room temperature by 15 changes of nitrogen. Then 2-propanol (20 ml) was added by cannula. The flask tap was closed and the flask swirled until the starting solids dissolved. The result was an orange-coloured supernatant and a dark solid. The flask tap was re-opened, a current of nitrogen fed in, and the flask contents heated at 60° C. for 2 h 5 min. The catalyst was checked at 30 min intervals. At each interval it was a dark brown solution, with a black solid at the bottom.

(b) Hydrogenation

The acetophenone was dissolved in 2-propanol (80 ml) then degassed for 40 min. This solution was added to the catalyst-containing flask by cannula, followed via syringe by the degassed 0.1M solution of KOH in 2-propanol. The mixture was left at room temperature, samples being taken at intervals and examined by gas chromatography. At the small scale of operation the reaction mixture was not sparged with the nitrogen, but sparging would be used in larger scale production. Results for production of (R)-1-phenylethanol were:

| | conversion % | ee % |
|---|---|---|
| 1 h | 92 | 84 |

The turnover number, integrated over 1 h was 189 $h^{-1}$.

EXAMPLE 2

| Reactant | Wt used | Mol wt | mol ratio | |
|---|---|---|---|---|
| $[Rh(Cp^*)Cl_2]_2$ | 6.2 mg | 618.08 | 1.0 | 10.1 µmol |
| (1R,2S)-(+)-cis-1-amino-2-indanol | 1.64 mg | 149.19 | 1.09 | 11 µmol |
| acetophenone | 2.06 g | 120.15 | 1547 | 17 mmol |
| 2-propanol | | | 129974 | |

(a) Catalyst Preparation

The rhodium compound and (1R,2S)-(+)-cis-2-aminoindanol were suspended in degassed 2-propanol (50 ml) under nitrogen, heated to 60° C. and held at 60° C. for 1 h, then cooled to ambient temperature. The resulting orange-red solution of the catalyst: [(+)-cis-(1R)-amino-(2S)-hydroxyindanyl]-[(mu5)-pentamethylcyclopentadienyl]-rhodium chloride was passed to the next stage but could be stored under argon or nitrogen.

(b) Hydrogenation

The catalyst solution was added to a degassed 0.1M solution of KOH in 2-propanol, followed by a solution of acetophenone in 2-propanol. The mixture was stirred at ambient temperature under nitrogen for 2 h, then worked up by neutralising with dilute hydrochloric acid and concentrating by vacuum distillation. The residue was diluted with ethyl acetate and washed with an equal volume of saturated aqueous sodium chloride. The organic layer was separated, dried over magnesium sulphate, separated from the solid and freed of solvent to give crude (S)-1-phenylethanol (1.76 g). Yield 84%, ee 89%. The turnover number, integrated over 1 h, was 324 $h^{-1}$.

EXAMPLE 3

| Reactant | Wt used | Mol wt | mol ratio | |
|---|---|---|---|---|
| $[Rh(Cp^*)Cl_2]_2$ | 6.3 mg | 618.08 | 1.0 | 10.2 µmol |
| (1S,2R)-(−)-cis-1-amino-2-indanol | 3.1 mg | 149.19 | 2.0 | 20.8 µmol |
| acetophenone | 1.29 g | 120.15 | 1039 | 10.6 mmol |
| 2-propanol | | | 63857 | |

(a) Catalyst Preparation

The rhodium compound was suspended in 50 ml of 2-propanol and degassed by 3 cycles of vacuum and nitrogen flush. The mixture was heated to gentle reflux until the solid dissolved, then cooled to ambient temperature. (1S, 2R)-(−)-cis-1-amino-2-indanol was added to the solution with stirring. The mixture was degassed by cycles of vacuum and nitrogen flush and warmed at 30° C. for 30 min. The resulting orange-red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation

The acetophenone was added to the catalyst solution. The mixture was stirred at ambient temperature for 1 h. Sodium 2-propoxide (0.25 ml of freshly prepared 0.1M solution in 2-propanol) was added. The mixture was stirred for 2 h and sampled; 57% of the acetophenone had reacted to give (R)-1-phenylethanol of 79% ee. The turnover number, integrated over 1 h, was 241 h$^{-1}$.

EXAMPLE 4

| Reactant | Wt used | Mol wt | mol ratio | |
| --- | --- | --- | --- | --- |
| [Ir(Cp*)Cl$_2$]$_2$** | 7.1 mg | 796.71 | 1.0 | 8.9 μmol |
| (1R,2S)-(+)-cis-1-amino-2-indanol | 1.64 mg | 149.19 | 1.23 | 11 μmol |
| acetophenone | 2.06 g | 120.15 | 1908 | 17 mmol |
| 2-propanol | | | 146550 | |

**purchased from STREM Chemicals (a) Catalyst Preparation

The Iridium compound and (1R,2S)-(+)-cis-1-amino-2-indanol were suspended in degassed 2-propanol (50 ml) under nitrogen, heated to 60° C. and held at 60° C. for 1 h, then cooled to ambient temperature. The resulting orange-red solution of the catalyst: [(+)-cis-(1R)-amino-(2S)-hydroxyindanyl]-[(mu5)-pentamethylcyclopentadienyl]-iridium chloride was passed to the next stage but could be stored under argon or nitrogen.

(b) Hydrogenation

To the catalyst solution was added a degassed 0.1M solution of KOH in 2-propanol, followed by a solution of acetophenone in 2-propanol. The mixture was warmed to 60° C. and stirred at ambient temperature under nitrogen for 1 h, then worked up by neutralising with dilute hydrochloric acid and concentrating by vacuum distillation. The residue was diluted with ethyl acetate and washed with an equal volume of saturated aqueous sodium chloride. The organic layer was separated, dried over magnesium sulphate, separated from the solid and freed of solvent to give crude (S)-1-phenylethanol (0.9 g). Yield 43%, ee 80%. The turnover number, integrated over 1 h, was 410 h$^{-1}$.

EXAMPLE 5

| Reactant | Wt used | Mol Wt | Mol ratio | |
| --- | --- | --- | --- | --- |
| [Rh(Cp*)Cl$_2$]$_2$ | 6.2 mg | 618.08 | 1.0 | 10 μmol |
| (1S,2R)-2-amino-1,2-diphenylethanol | 4.3 mg | 213.28 | 2.01 | 20.1 μmol |
| triethylamine | 7 μl | 101.19 | | |
| #Imine | 53 mg | 205.26 | 26 | 0.26 mmol |
| CF$_3$CO$_2$H | 20 μl | 114.02 | | 0.26 mmol |
| 2-propanol | 11 ml | | 144000 | |

Imine = 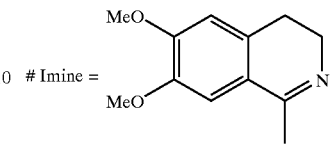

(a) Catalyst Preparation (1S,2R)-2-amino-1,2 diphenylethanol (Aldrich: 4.3 mg, 20.1 μmol) was dissolved in 2-propanol (10 ml) in a small vial with magnetic stirrer flushed with nitrogen. The rhodium compound (6.2 mg, 10 μmol) was added to the solution, together with triethylamine(7 μl). The solution was warmed to 60° C. for 45 min during which it turned brown. The resulting solution of the catalyst: [(1S)-amino-(2R)-hydroxydiphenylethyl]-[(mu5)-pentamethylcyclopentadienyl]-rhodium chloride was used directly in the following reaction.

(b) Hydrogenation

Iminium trifluoroacetate was prepared by adding trifluoroacetic acid (20 μl, 0.26 mmol) to the imine (53 mg, 0.26 mmol) in 2-propanol (1 ml). This solution was added to the catalyst solution and heated at 60° C. for 20 h. After quenching into aqueous acid, the aqueous solution was made basic before extracting into methylene chloride, the product was analysed by $^1$Hn.m.r. and found to be 54% of the desired product, the remainder was imine starting material.

EXAMPLE 6

| Reactant | Wt used | Mol wt | Mol ratio | |
| --- | --- | --- | --- | --- |
| [Rh(Cp*)Cl$_2$]$_2$ | 6.2 mg | 618.08 | 1.0 | 9.73 μmol |
| N-tosyl-(1S,2R)-cis-1-amino-2-indanol | 6.8 mg | 303.38 | 2.3 | 22.4 μmol |
| 2-propanol | 1 ml | | | |
| triethylamine | 7 μl | 101.19 | | |
| #Imine | 40 mg | 205.26 | | 0.195 mmol |
| CF$_3$CO$_2$H | 15 μl | | | 0.195 mmol |

(a) Catalyst Preparation

N-tosyl-(1S,2R)-cis-1-amino-2-indanol (6.8 mg, 22.41 μmol) was dissolved in 2-propanol (1 ml) in a small nitrogen flushed vial with magnetic stirrer. The rhodium compound (6.2 mg, 9.73 μmol) was added to the solution, which was then warmed to 60° C. for 1 h. Triethylamine (7 μl) was added. The solution colour changed from orange to purple. The solution was maintained at 60° C. for a further 20 min, then cooled to ambient temperature. The resulting solution of the catalyst: [N-tosyl-cis-(1S)-amino-(2R)-hydroxyindanyl]-[(mu5)-pentamethylcyclopentadienyl]-rhodium chloride was stored under nitrogen.

(b) Hydrogenation

The iminium trifluoroacetate was prepared by adding trifluoroacetic acid (15 μl, 0.195 mmol) to the imine (40 mg, 0.195 mmol) in 2-propanol (1 ml). The catalyst solution was added and the mixture heated at 60° C. for 16 h. After quenching into aqueous sodium bicarbonate and extracting into methylene chloride, the product was analysed by $^1$Hn.m.r. and found to be 42% of the desired product; the remainder was the imine starting material.

EXAMPLE 7

| Reactant | Wt used | Mol wt | | Mol Ratio |
|---|---|---|---|---|
| [Rh(Cp*)Cl$_2$]$_2$ | 6.3 mg | 618.08 | 1.0 | 10.2 μmol |
| N-Tosyl-(1R,2R)-1,2-diphenylethylenediamine | 7.3 mg | 366.48 | 1.93 | 20 μmol |
| triethylamine | 6 μl | 101.19 | 4.18 | 43 μmol |
| 2-propanol | 10 ml | 60.1 | | |
| CH$_3$CN | 6.4 ml | 41.05 | | |
| #Imine | 109 mg | 205.26 | | 0.53 mmol |
| triethylamine/formic acid 2:5 | 0.25 ml | | | |

(a) Catalyst Preparation

N-Tosyl-(1R,2R)-1,2-diphenylethylenediamine (7.3 mg, 20 μmol) and the rhodium compound (6.3 mg, 10.2 μmol) were suspended in 2-propanol (10 ml) in a small vial flushed with nitrogen. Triethylamine (6 μl) was added. The mixture was stirred at 55° C. until all the solid had dissolved and then heated to 80° C. for 30 min then cooled to ambient temperature. The resulting solution of the catalyst: [N-tosyl-(1R)-amino-(2R)-aminodiphenylethyl]-[(mu5)-pentamethylcyclopentadienyl]-rhodium chloride was stored under nitrogen.

(b) Hydrogenation [Substrate:Catalyst Ratio 266:1]

A portion (8 ml) of the above catalyst solution was placed into a vial and the solvent evaporated by applying vacuum. The residue was redissolved in acetonitrile (6.4 ml) and degassed with nitrogen. A nitrogen-purged vial was charged with the Imine (109 mg, 0.53 mmol) and 0.8 ml of the catalyst solution followed by a 2:5 triethylamine:formic acid mixture (0.25 ml). The mixture was heated at 60° C. for 1 h, quenched by addition of water and then extracted into methylene chloride, dried over magnesium sulfate and the crude product analysed by $^1$HNMR that showed it to be >95% of the desired amine. Chiral shift $^1$Hn.m.r. showed the amine to be 74.8% ee.

EXAMPLE 8

| Reactant | Wt used | Mol wt | | mol ratio |
|---|---|---|---|---|
| [Rh(Cp*)Cl$_2$]$_2$ | 6 mg | 618.08 | 1.0 | 9.7 μmol |
| (1S,2R)-(-)-cis-1-amino-2-indanol | 3.2 mg | 149.19 | 2.1 | 22.1 μmol |
| acetophenone | 0.126 g | 120.15 | | 1 mmol |
| 2-butanol | 20 ml | 74.12 | | 0.22 mol |

(a) Catalyst Preparation

The rhodium compound and (1S,2R)-(-)-cis-1-amino-2-indanol were suspended in degassed 2-butanol (20 ml) under nitrogen, and the reaction purged with nitrogen for 30 minutes. The yellow mixture was heated to 35° C. for 0.5 h, during which time the colour intensified to orange/red, then cooled to ambient temperature. The resulting orange-red solution of the catalyst: [(-)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 539:1]

Acetophenone (0.126 g, 1 mmol) was added to a dry vial. Then a portion (2 ml) of the catalyst solution was added followed by sodium 2-propoxide solution (25 μl of 0.2M solution in 2-propanol). The mixture was stirred at ambient temperature under nitrogen for 2 h. This gave (R)-1-phenylethanol Yield 66.2%, ee 87%. The initial turnover number, integrated over 1 h, was 574 h$^{-1}$.

EXAMPLE 9

| Reactant | Wt used | Mol wt | | mol ratio |
|---|---|---|---|---|
| [Rh(Cp*)Cl$_2$]$_2$ | 6.1 mg | 618.08 | 1.0 | 9.9 μmol |
| (1S,2R)-(-)-cis-1-amino-2-indanol | 3 mg | 149.19 | 2.03 | 20 μmol |
| acetophenone | 1.089 g | 120.15 | | 9.1 mmol |
| 2-butanol | 20 ml | 74.12 | | 0.22 mol |

(a) Catalyst Preparation

The rhodium compound and (1S,2R)-(-)-cis-1-amino-2-indanol were suspended in degassed 2-butanol (20 ml) under nitrogen, and the reaction purged with nitrogen for 30 minutes. The yellow mixture was heated to 35° C. for 20 min, during which time the colour intensified to orange/red, then cooled to ambient temperature. The resulting orange-red solution of the catalyst: [(-)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 460:1]

Sodium 2-propoxide (0.45 ml of 0.2M solution in 2-propanol) was charged to the catalyst solution. After 2 minutes, the acetophenone (1.0889 g, 9.1 mmol) was added. The mixture was stirred under vacuum at 35° C. for 1.5 h, then heated to maintain a temperature between 40–45° C. for 4 hours. This gave (R)-1-phenylethanol Yield 87.1%, ee 87%. The turnover number, integrated over 1 h, was 1502 h$^{-1}$.

EXAMPLE 10

| Reactant | Wt used | Mol wt | | mol ratio |
|---|---|---|---|---|
| [Rh(Cp*)Cl$_2$]$_2$ | 5.9 mg | 618.08 | 1.0 | 9.57 μmol |
| (1S,2R)-(-)-cis-1-amino-2-indanol | 3.1 mg | 149.19 | 2.17 | 20.8 μmol |
| α-tetralone | 0.5 ml | 146.19 | 393 | 3.76 mmol |
| 2-propanol | 50 ml | 60.1 | | 0.653 mol |

(a) Catalyst Preparation

The rhodium compound and (1S,2R)-(-)-cis-1-amino-2-indanol were suspended in degassed 2-propanol (50 ml) under nitrogen, and the reaction purged with nitrogen for 30 minutes. The mixture was heated to 35° C. for 10 min. The resulting orange solution of the catalyst: [(-)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation

Sodium 2-propoxide (0.38 ml of 0.1M solution in 2-propanol) was charged to the catalyst solution followed by the α-tetralone (0.5 ml, 3.76 mmol). The mixture was stirred under vacuum (80 mmHg) at 35° C. for 2 h, after the first hour the flask was back filled with nitrogen and sufficient 2-propanol charged to compensate for the volume removed by distillation. This gave (R)-1-tetralol Yield 98.4%, ee 95.7%. The turnover number, integrated over 1 h, was 185 h$^{-1}$

EXAMPLE 11

| Reactant | Wt used | Mol wt | mol ratio | |
|---|---|---|---|---|
| [Rh(Cp*)Cl$_2$]$_2$ | 24.4 mg | 618.08 | 1.0 | 39.48 μmol |
| (1R,2S)-(−)-norephedrine | 12.1 mg | 151.21 | 2.03 | 80 μmol |
| α-tetralone | 5 ml | 146.19 | 952 | 37.6 mmol |
| 2-propanol | 125 ml | 60.1 | | 1.63 mol |

(a) Catalyst Preparation

The rhodium compound and (1R,2S)-(−)-norephedrine were suspended in degassed 2-propanol (75 ml) under nitrogen, and the reaction purged with nitrogen for 30 minutes. The mixture was heated to 35° C. for 30 min. The resulting orange solution of the catalyst: [(−)-(1R,2S)-norephedrinyl]-[(mu5)-pentamethylcyclopentadienyl]-rhodiumchloride was passed to the next stage but could be stored under argon or nitrogen.

(b) Hydrogenation

Sodium 2-propoxide (1.55 ml of 0.1M solution in 2-propanol) was charged to the catalyst solution and the pressure reduced (40–80 mmHg). The α-tetralone (5 ml, 37.6 mmol) in 2-propanol (75 ml) was then added over a period of 15 min. The mixture was stirred under vacuum (40–80 mmHg) at 35° C. for 4 h, at hourly intervals the flask was back filled with nitrogen and sufficient 2-propanol charged to compensate for the volume removed by distillation. This gave (S)-1-tetralol Yield 96%, ee 96.2%. The turnover number, integrated over 1 h, was 382 h$^{-1}$.

EXAMPLE 12

| Reactant | Wt used | Mol wt | mol ratio | |
|---|---|---|---|---|
| [Rh(Cp*)Cl$_2$]$_2$ | 26.4 mg | 618.08 | 1.0 | 42.7 μmol |
| (1S,2R)-(−)-cis-1-amino-2-indanol | 13.4 mg | 149.19 | 2.1 | 89.8 μmol |
| acetophenone | 5 ml | 120.15 | | 42.9 mmol |
| 2-propanol | 270 ml | | | |

(a) Catalyst Preparation

The rhodium compound and (1S,2R)-(−)-cis-1-amino-2-indanol were suspended in degassed 2-propanol (20 ml) under nitrogen, and the reaction purged with nitrogen for 30 minutes. The mixture was heated to 40–50° C. for 30 min, during which time the colour intensified to deep red, then cooled to ambient temperature. The resulting red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 5018:1]

Acetophenone (5 ml, 42.9 mmol) was added to a dry Schlenck flask containing 250 ml 2-propanol. Then a portion (2 ml) of the catalyst solution was added followed by sodium 2-propoxide solution (0.3 ml of 0.1 M solution in 2-propanol). The mixture was stirred at 18° C. under vacuum (28 mmHg) for 5 h. This gave (R)-1-phenylethanol Yield 74%, ee 86.8%. The initial turnover number, integrated over 1 h, was 1947 h$^{-1}$.

EXAMPLE 13

| Reactant | Wt used | Mol wt | mol ratio | |
|---|---|---|---|---|
| [Rh(Cp*)Cl$_2$]$_2$ | 6.2 mg | 618.08 | 1.0 | 10 μmol |
| (1S,2R)-(−)-cis-1-amino-2-indanol | 4.3 mg | 149.19 | 2.88 | 28.8 μmol |
| p-methylacetophenone | 0.280 g | 134.18 | | 2.1 mmol |
| 2-propanol | | | | |

(a) Catalyst Preparation

The rhodium compound and (1S,2R)-(−)-cis-1-amino-2-indanol were suspended in degassed 2-propanol (10 ml) under nitrogen, and the reaction purged with nitrogen for 30 minutes. The mixture was heated to 90° C. for 20 min, during which time the colour intensified to orange/red, then cooled to ambient temperature. The resulting orange-red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 523:1]

p-Methylacetophenone (0.28 g, 2.1 mmol) was added to a dry vial. Then a portion (2 ml) of the catalyst solution was added followed by sodium 2-propoxide solution (90 μl of 0.1M solution in 2-propanol). The mixture was stirred at ambient temperature under nitrogen for 2 h. This gave 1-(p-methylphenyl)ethanol Yield 56.8%, ee 56%. The initial turnover number, integrated over 1 h, was 1064 h$^{-1}$.

EXAMPLE 14

| Reactant | Wt used | Mol wt | mol ratio | |
|---|---|---|---|---|
| [Rh(Cp*)Cl$_2$]$_2$ | 6.2 mg | 618.08 | 1.0 | 10 μmol |
| (1S,2R)-(−)-cis-1-amino-2-indanol | 4.3 mg | 149.19 | 2.88 | 28.8 μmol |
| p-trifluoromethyl-acetophenone | 0.384 g | 188.15 | | 2 mmol |
| 2-propanol | | | | |

(a) Catalyst Preparation

The rhodium compound and (1S,2R)-(−)-cis-1-amino-2-indanol were suspended in degassed 2-propanol (10 ml) under nitrogen, and the reaction purged with nitrogen for 30 minutes. The mixture was heated to 90° C. for 20 min, during which time the colour intensified to orange/red, then cooled to ambient temperature. The resulting orange-red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 498:1]

p-Trifluoromethylacetophenone (0.384 g, 2 mmol) was added to a dry vial. Then a portion (2 ml) of the catalyst solution was added followed by sodium 2-propoxide solution (90 μl of 0.1M solution in 2-propanol). The mixture was stirred at ambient temperature under nitrogen for 2 h. This gave 1-(p-trifluoromethylphenyl)ethanol Yield 96.7%, ee 73.8%. The initial turnover number, integrated over 1 h, was 412 h$^{-1}$.

EXAMPLE 15

| Reactant | Wt used | Mol wt | mol ratio | |
|---|---|---|---|---|
| [Rh(Cp*)Cl₂]₂ | 6.2 mg | 618.08 | 1.0 | 10 μmol |
| (1S,2R)-(−)-cis-1-amino-2-indanol | 3.3 mg | 149.19 | 2.2 | 22.1 μmol |
| p-chloroacetophenone | 0.162 g | 154.6 | 517 | 1.05 mmol |
| 2-propanol | | | | |

(a) Catalyst Preparation

The rhodium compound and (1S,2R)-(−)-cis-1-amino-2-indanol were suspended in degassed 2-propanol (10 ml) under nitrogen, and the reaction purged with nitrogen for 30 minutes. The mixture was heated to 90° C. for 20 min, during which time the colour intensified to orange/red, then cooled to ambient temperature. The resulting orange-red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 524:1]

p-Chloroacetophenone (0.162 g, 1.05 mmol) was added to a dry vial. Then a portion (2 ml) of the catalyst solution was added followed by sodium 2-propoxide solution (50 μl of 0.1M solution in 2-propanol). The mixture was stirred at ambient temperature under nitrogen for 19 h. This gave 1-(p-chlorophenyl)ethanol Yield 90.6%, ee 71.6%. The initial turnover number, integrated over 1 h, was 846 h⁻¹.

EXAMPLE 16

| Reactant | Wt used | Mol wt | mol ratio | |
|---|---|---|---|---|
| [Rh(Cp*)Cl₂]₂ | 6.2 mg | 618.08 | 1.0 | 10 μmol |
| (1S,2R)-(−)-cis-1-amino-2-indanol | 3.3 mg | 149.19 | 2.2 | 22.1 μmol |
| o-chloroacetophenone | 0.160 g | 154.6 | | 1 mmol |
| 2-propanol | | | | |

(a) Catalyst Preparation

The rhodium compound and (1S,2R)-(−)-cis-1-amino-2-indanol were suspended in degassed 2-propanol (10 ml) under nitrogen, and the reaction purged with nitrogen for 30 minutes. The mixture was heated to 90° C. for 20 min, during which time the colour intensified to orange/red, then cooled to ambient temperature. The resulting orange-red solution of the catalyst: [(−)-cis-(1S)-amino-(2R)-hydroxyindanyl]-[(mu5)-pentamethylcyclopentadienyl]-rhodiumchloride was passed to the next stage but could be stored under argon or nitrogen.

(b) Hydrogenation [Substrate:Catalyst Ratio 517:1]

o-Chloroacetophenone (0.16 g, 1 mmol) was added to a dry vial. Then a portion (2 ml) of the catalyst solution was added followed by sodium 2-propoxide solution (50 μl of 0.1M solution in 2-propanol). The mixture was stirred at ambient temperature under nitrogen for 19 h. This gave 1-(o-chlorophenyl)ethanol Yield 94.3%, ee 69.1 %. The turnover number, integrated over 1 h, was 195 h⁻¹.

EXAMPLE 17

| Reactant | Wt used | Mol wt | mol ratio | |
|---|---|---|---|---|
| [Ir(Cp*)Cl₂]₂ | 32.8 mg | 796.67 | 1.0 | 41.2 μmol |
| (1S,2R)-(+)-norephedrine | 20 mg | 151.21 | 3.2 | 132 μmol |
| acetophenone | 2 ml | 120.15 | 413 | 17 mmol |
| 2-propanol | 100 ml | | | |

(a) Catalyst Preparation

The iridium compound and (+)-norephedrine were suspended in degassed 2-propanol (20 ml) under nitrogen, and the reaction purged with nitrogen for 30 minutes. The mixture was heated to 60° C. for 90 min, then cooled to ambient temperature. The resulting solution of the catalyst: [(+)-(1S,2R)-norephedrinyl]-[(mu5)-pentamethylcyclopentadienyl]-iridium chloride was passed to the next stage but could be stored under argon or nitrogen.

(b) Hydrogenation

Acetophenone (2 ml, 17 mmol) was dissolved in 2-propanol (80ml) and purged with nitrogen. Then the catalyst solution was added followed by potassium hydroxide solution (3.3 ml of 0.1M solution in 2-propanol). The mixture was stirred at ambient temperature under nitrogen for 10 h. This gave 1-phenylethanol Yield 68%, ee 49%. The initial turnover number, integrated over 1 h, was 318 h⁻¹.

EXAMPLE 18

| Reactant | Wt used | Mol wt | mol ratio | |
|---|---|---|---|---|
| [Rh(Cp*)Cl₂]₂ | 1 g | 618.08 | 1.0 | 1.62 mmol |
| (1S,2R)-(−)-cis-1-amino-2-indanol | 0.5 g | 149.19 | 2.08 | 3.36 mol |
| tetralone | 200 ml | 146.19 | 928 | 1.5 mol |
| 2-propanol | 10 l | | | |

(a) Catalyst Preparation

2-Propanol (9.5 l) was charged to a 20 l reaction flask which was deoxygenated and back-filled with nitrogen. The rhodium compound and (1S,2R)-(−)-cis-2-aminoindanol were charged to the vessel with stirring and the mixture was deoxygenated and back-filled with nitrogen. The orange suspension was heated to 35° C. until a clear red solution of the catalyst: [(−)-cis-(1S)-amino-(2R)-hydroxyindanyl]-[(mu5)-pentamethylcyclopentadienyl]-rhodiumchloride was formed.

(b) Hydrogenation

Tetralone (200 ml, 1.5 mol) was charged to the catalyst solution, followed by 2-propanol (0.5 l). The pressure was reduced (28.5 mmHg) and then a sodium 2-propoxide solution (120ml of 0.1M solution in 2-propanol) was charged. The mixture was stirred at ambient temperature under nitrogen for 4.5 h, at hourly intervals the flask was back filled with nitrogen and sufficient 2-propanol charged to compensate for the volume removed by distillation. This gave (R)-1-tetralol Yield 96.9%, ee 86.9%. The turnover number, integrated over 1 h, was 358 h⁻¹.

EXAMPLE 19

| Reactant | Wt used | Mol wt | | mol ratio |
|---|---|---|---|---|
| [Rh(Cp*)Cl$_2$]$_2$ | 1 g | 618.08 | 1.0 | 1.62 mmol |
| (1S,2R)-(−)-cis-1-amino-2-indanol | 0.49 g | 149.19 | 2.04 | 3.31 mol |
| acetophenone | 179 g | 120.15 | 920 | 1.49 mol |
| 2-propanol | 10 l | | | |

(a) Catalyst Preparation

2-Propanol (9.5 l) was charged to a 20 l reaction flask which was deoxygenated and back-filled with nitrogen. The rhodium compound and (1S,2R)-(−)-cis-1-amino-2-indanol were charged to the vessel with stirring and the mixture was deoxygenated and back-filled with nitrogen. The orange suspension was heated to 35° C. until a clear red solution of the catalyst: [(−)-cis-(1S)-amino-(2R)-hydroxyindanyl]-[(mu5)-pentamethylcyclopentadienyl]-rhodiumchloride was formed.

(b) Hydrogenation

Acetophenone (200 ml, 1.5 mol) was charged to the catalyst solution, followed by 2-propanol (0.5 l). The pressure was reduced (28.5 mmHg) and then a sodium 2-propoxide solution (120 ml of 0.1M solution in 2-propanol) was charged. The mixture was stirred at ambient temperature under nitrogen for 2.5 h, at hourly intervals the flask was back filled with nitrogen and sufficient 2-propanol charged to compensate for the volume removed by distillation. This gave (R)-1-phenylethanol Yield 99.6%, ee 82.9%. The turnover number, integrated over 1 h, was 454 h$^{-1}$.

EXAMPLE 20

| Reactant | Wt used | Mol wt | | mol ratio |
|---|---|---|---|---|
| [Rh(Cp*)Cl$_2$]$_2$ | 6.3 mg | 618.08 | 1.0 | 10 μmol |
| (1R,2S)-(−)-2-amino-1,2-diphenyl-ethanol | 4.5 mg | 213.28 | 2.07 | 21.1 μmol |
| acetophenone | 0.120 g | 120.15 | 490 | 0.99 mmol |
| 2-propanol | | | | |

(a) Catalyst Preparation

The rhodium compound and (1R,2S)-(−)-2-amino-1,2-diphenylethanol were suspended in degassed 2-propanol (20 ml) under nitrogen, and the reaction purged with nitrogen for 30 minutes. The mixture was heated to 80° C. for 30 min, then cooled to ambient temperature. The resulting solution of the catalyst: [(−)-(2S)-amino-(1R)-hydroxydiphenylethyl]-[(mu5)-pentamethylcyclopentadienyl]-rhodiumchloride was passed to the next stage but could be stored under argon or nitrogen.

(b) Hydrogenation

Acetophenone (0.12 g, 0.99 mmol) was added to a dry vial. Then a portion (2 ml) of the catalyst solution was added followed by sodium 2-propoxide solution (50 μl of 0.1M solution in 2-propanol). The mixture was stirred at ambient temperature under nitrogen for 2 h. This gave 1-phenylethanol Yield 90.7%, ee 66%. The turnover number, integrated over 1 h, was 826 h$^{-1}$.

EXAMPLE 21

| Reactant | Wt used | Mol wt | | mol ratio |
|---|---|---|---|---|
| [Rh(Cp*)Cl$_2$]$_2$ | 6.2 mg | 618.08 | 1.0 | 10.4 μmol |
| (S)-(+)-2-amino-1-phenylethanol | 2.7 mg | 137.18 | 1.96 | 19.7 μmol |
| acetophenone | 0.140 g | 120.15 | | 1.17 mmol |
| 2-propanol | | | | |

(a) Catalyst Preparation

The rhodium compound and (S)-(+)-2-amino-1-phenylethanol were suspended in degassed 2-propanol (20 ml) under nitrogen, and the reaction purged with nitrogen for 30 minutes. The mixture was heated to 80° C. for 30 min, then cooled to ambient temperature. The resulting solution of the catalyst: [(+)-(2)-amino-(1S)-hydroxyphenylethyl]-[(mu5)-pentamethylcyclopentadienyl]-rhodiumchloride was passed to the next stage but could be stored under argon or nitrogen.

(b) Hydrogenation [Substrate:Catalyst Ratio 580:1]

Acetophenone (0.14 g, 1.17 mmol) was added to a dry vial. Then a portion (2 ml) of the catalyst solution was added followed by sodium 2-propoxide solution (50 μl of 0.1M solution in 2-propanol). The mixture was stirred at ambient temperature under nitrogen for 2 h. This gave 1-phenylethanol Yield 62.4%, ee 77.4%. The initial turnover number, integrated over 1 h, was 487 h$^{-1}$.

What is claimed is:

1. A process for the transfer hydrogenation of a compound of formula (1) to produce a compound of formula (2):

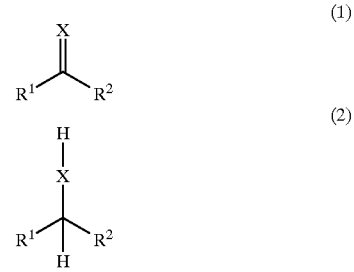

wherein:

X represents CR$^3$R$^4$, NR$^5$, (NR$^5$R$^6$)$^+$Q$^-$, O or S;

R$^1$, R$^2$, R$^3$, R$^4$, R$^5$ and R$^6$ each, independenly, represent a hydrogen atom, an optionally substituted hydrocarbyl, a perhalogenated hydrocarbyl or an optioally substituted heterocyclyl group, one or more of R$^1$ and R$^2$, R$^1$ and R$^3$, R$^2$ and R$^4$, R$^3$ and R$^4$, R$^1$ and R$^5$, R$^2$ and R$^6$ and R$^5$ and R$^6$ optionally being linked in such a way as to form an optionally substituted ring(s); and Q$^-$ represents an anion;

Said process comprising reacting the compound of formula (1) with a hydrogen donor in the presence of a catalyst, wherein the catalyst has the general formula:

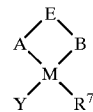

wherein:

R$^7$ represents an optionally substituted cyclopentadienyl group;

A represents —NR$^8$—, —NR$^9$—, —NHR$^8$ or —NR$^8$R$^9$ where R$^8$ is H, C(O)R$^{10}$, SO$_2$R$^{10}$, C(O)NR$^{10}$R$^{14}$, C(S)NR$^{10}$R$^{14}$, C(=NR$^{14}$)SR$^{15}$ or C(=NR$^{14}$)OR$^{15}$, R$^9$ and R$^{10}$ each independently represents an optionally substituted hydrocarbyl, perhalogenated hydrocarbyl or an optionally substituted heretocyclyl group, and R$^{14}$ and R$^{15}$ are each independently hydrogen or a group as defined for R$^{10}$;

B represents —O—, —OH, OR$^{11}$, —S—, —SH, SR$^{11}$, —NR$^{11}$—, —NR$^{12}$—, —NHR$^{12}$ or —NR$^{11}$R$^{12}$ where R$^{12}$ is H, C(O)R$^{13}$, SO$_2$R$^{13}$, C(O)NR$^{13}$R$^{16}$, C(S)NR$^{13}$R$^{16}$, C(=NR$^{16}$)SR$^{17}$ or C(=NR$^{16}$)OR$^{17}$, R$^{11}$ and R$^{13}$ each independently represents an optionally substituted hydrocarbyl, perhalogenated hydrocarbyl or an optionally substituted heterocyclyl group, and R$^{16}$ and R$^{17}$ are each independently hydrogen or a group as defined for R$^{13}$;

E represents a linking group wherein A and B are linked through 2, 3 or 4 carbon atoms, said carbon atoms being unsubstituted or substituted;

M represents a group VIII transition metal; and

Y represents an anionic group, a basic ligand or a vacant site;

provided that when Y is not a vacant site that at least one of A or B is substituted with a hydrogen atom.

2. A process according to claim 1, in which the compound of formula (1) is a ketone, an imine or an iminium salt.

3. A process according to claim 1, wherein M is ruthenium, rhodium or iridium.

4. A process according to claim 1, wherein R$^7$ is a cyclopendadienyl group substituted with between 3 and 5 substitutents.

5. A process according to claim 1, wherein the compound of formula (1) is prochiral and the catalyst is chiral, an enantiomerically purified form of the catalyst being employed, whereby the compound of formula (1) is asymmetrically hydrogenated.

6. A process according to claim 1 in which A—E—B contains at least one stereospecific centre.

7. A process according to claim 1, in which the hydrogen donor is selected from hydrogen, primary and secondary alcohols, primary and secondary amines, carboxylic acids and their esters and amine salts, cyclohexadine, cyclohexene, tetralin, dihydrofuran, terpenes, reducing agents with a reduction potential of greater than –0.1 eV and any combination thereof.

8. A process according to claim 7, in which the hydrogen donor is propan-2-ol, butan-2-ol or a mixture of triethylamine and formic acid.

9. A process according to claim 1, in which the products from dehydrogenation of the hydrogen donor are removed by vacuum distillation.

10. A process according to claim 1, in which the process is carried out in presence of a based having a pK$_a$ of at least 8.0.

11. A process according to claim 4, wherein R$^7$ is substituted with 5 substituents.

12. A process according to claim 7, wherein R$^7$ is a pentamethylcyclopentadienyl group.

13. A process according to claim 1, wherein B is O, OH, OR$^{11}$, NR$^{11}$, NR$^{12}$, NHR$^{12}$ or NR$^{11}$R$^{12}$.

14. A process according to any one claims 2, 3, 4, or 5 wherein R$^7$ is a cyclopentadienyl group substituted with between 3 and 5 substituents.

15. A process according to claim 1 or claim 13, wherein either or both of A and B, when an amino group, is substituted with an acyl or sulfonyl group.

16. A process according to claim 1 or claim 13, wherein when B is O, OH, or OR$^{11}$, A and B are linked through 2 or 3 carbon atoms, and when B is NR$^{11}$, NR$^{12}$, NHR$^{12}$ or NR$^{11}$R$^{12}$, A and B are linked through 2 carbon atoms.

17. A process according to claim 1 or claim 13, in which a ketone of formula (1) is transfer hydrogentated in the presence of a catalyst wherein B is O, OH, or OR$^{11}$.

18. A process according to claim 1 or claim 13, in which an imine or iminium salt of formula (1) is transfer hydrogentated in the presence of catalyst wherein A is NR$^8$, NR$^8$, NHR$^8$ or NR$^8$R$^9$; B is NR$^{11}$, NR$^{12}$, or NR$^{11}$R$^{12}$, and at least one of A or B having a R$^8$ or R$^{12}$ group which is a tosyl group.

19. A process according to claim 1 or claim 13, in which A—E—B is one of the following:

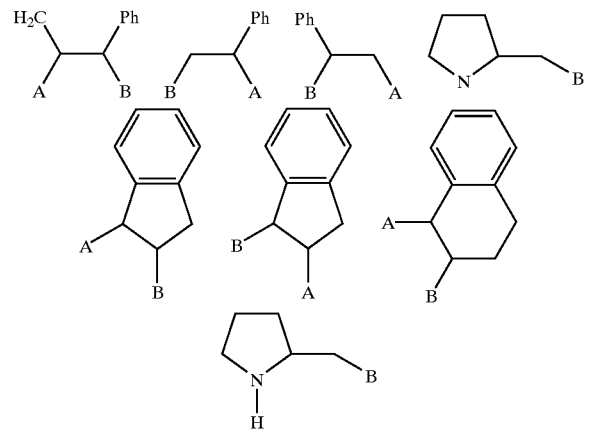

wherein A represents NR$^8$ or NHR$^8$, R$^8$ is hydrogen, and B represents O or OH.

20. A process according to claim 1 or claim 13, in which A—E—B is one of the following:

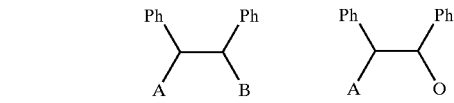

wherein A represents NR$^8$ or NHR$^8$, R$^8$ is hydrogen, and B represents NR$^{12}$ or NHR$^{12}$, R$^{12}$ is hydrogen or tosyl.

21. A process according to claim 14, wherein R$^7$ is substituted with 5 substituents.

22. A process according to claim 21, wherein R$^7$ is a pentamethylcyclopentadienyl group.

* * * * *